US012569558B2

(12) United States Patent
Shi et al.

(10) Patent No.: US 12,569,558 B2
(45) Date of Patent: Mar. 10, 2026

(54) COMPOSITE ADJUVANT SYSTEM AND METHOD FOR PREPARING ADJUVANT

(71) Applicant: IMMUNE-PATH BIOTECHNOLOGY (SUZHOU) CO., LTD., Jiangsu (CN)

(72) Inventors: Li Shi, Shanghai (CN); Zhi Zhang, Shanghai (CN); Wenli Tian, Shanghai (CN); Zhihao Li, Shanghai (CN); Chengren Shen, Shanghai (CN)

(73) Assignee: IMMUNE-PATH BIOTECHNOLOGY (SUZHOU) CO., LTD., Jiangsu (CN)

( * ) Notice: Subject to any disclaimer, the term of this patent is extended or adjusted under 35 U.S.C. 154(b) by 1077 days.

(21) Appl. No.: 17/623,489

(22) PCT Filed: Jun. 24, 2020

(86) PCT No.: PCT/CN2020/098012
§ 371 (c)(1),
(2) Date: Dec. 28, 2021

(87) PCT Pub. No.: WO2020/259557
PCT Pub. Date: Dec. 30, 2020

(65) Prior Publication Data
US 2022/0331424 A1      Oct. 20, 2022

(30) Foreign Application Priority Data
Jun. 28, 2019    (CN) ........................ 201910574668.X

(51) Int. Cl.
*A61K 39/39* (2006.01)
*A61K 39/00* (2006.01)

(52) U.S. Cl.
CPC .... *A61K 39/39* (2013.01); *A61K 2039/55505* (2013.01); *A61K 2039/55561* (2013.01)

(58) Field of Classification Search
None
See application file for complete search history.

(56) References Cited

FOREIGN PATENT DOCUMENTS

| CN | 101534854 A | 9/2009 |
| CN | 101971030 A | 2/2011 |
| CN | 102188701 A | 9/2011 |
| CN | 103471902 A | 12/2013 |
| CN | 104634959 A | 5/2015 |
| CN | 106729702 A | 5/2017 |
| CN | 107929729 A | 4/2018 |
| CN | 109432418 A | 3/2019 |

(Continued)

OTHER PUBLICATIONS

Garcon N, Friede M. Evolution of Adjuvants Across the Centuries. In: Plotkin S, Orenstein W, Offit P, Edwards K, eds. Plotkin's Vaccines (Seventh Edition). Elsevier; 2018:61-74.e4 (Year: 2018).*

(Continued)

*Primary Examiner* — Joanne Hama
*Assistant Examiner* — Hannah Sunshine
(74) *Attorney, Agent, or Firm* — IP & T GROUP LLP

(57) ABSTRACT

Present disclosure is a new adjuvant system containing an aluminum phosphate adjuvant and a CpG adjuvant and the preparation method thereof.

8 Claims, 3 Drawing Sheets

(56)                    References Cited

FOREIGN PATENT DOCUMENTS

WO         2010/109323  A1      9/2010
WO         2019/016654  A1      1/2019

OTHER PUBLICATIONS

Aebig JA, Mullen GE, Dobrescu G, et al. Formulation of vaccines containing CpG oligonucleotides and alum. J Immunol Methods. 2007;323(2):139-146 (Year: 2007).*

InvivoGen "B-Class TLR9 Agonist Kit" 14B07-MM datasheet, Feb. 2011 (Year: 2011).*

Burrell LS, Johnston CT, Schulze D, Klein J, White JL, Hem SL. Aluminium phosphate adjuvants prepared by precipitation at constant pH. Part I: composition and structure. Vaccine. 2000;19(2-3):275-281 (Year: 2001).*

Clapp T, Siebert P, Chen D, Jones Braun L. Vaccines with aluminum-containing adjuvants: optimizing vaccine efficacy and thermal stability. J Pharm Sci. 2011;100(2):388-401 (Year: 2010).*

HogenEsch H, O'Hagan DT, Fox CB. Optimizing the utilization of aluminum adjuvants in vaccines: you might just get what you want. NPJ Vaccines. 2018;3:51 (Year: 2018).*

Iyer S, HogenEsch H, Hem SL. Effect of the degree of phosphate substitution in aluminum hydroxide adjuvant on the adsorption of phosphorylated proteins. Pharm Dev Technol. 2003;8(1):81-86 (Year: 2003).*

Jendrek S, Little SF, Hem S, Mitra G, Giardina S. Evaluation of the compatibility of a second generation recombinant anthrax vaccine with aluminum-containing adjuvants. Vaccine. 2003;21(21-22):3011-3018 (Year: 2003).*

Temperton NJ, Quenelle DC, Lawson KM, et al. Enhancement of humoral immune responses to a human cytomegalovirus DNA vaccine: adjuvant effects of aluminum phosphate and CpG oligodeoxynucleotides. J Med Virol. 2003;70(1):86-90 (Year: 2003).*

Thakkar SG, Zhengrong C. Methods to Prepare Aluminum Salt-Adjuvanted Vaccines. In: Fox CB, ed. Vaccine Adjuvants: Methods and Protocols. Humana Press: Springer; 2017 (Year: 2016).*

Mostafa MM, Al-Ghobashy MA, Fathalla FA, Salem MY. Optimization and validation of ELISA immunoassay for the evaluation of in-vitro relative potency of a four-component human papillomavirus vaccine products. Biologicals. 2016;44(6):596-599. (Year: 2016).*

First Office Action of priority document CN 201910574668.X on Sep. 9, 2021.

* cited by examiner

Samples from left to right: AP (PI=9.0) 1-5、AH 1-5          Samples from left to right: Marker (5ul)、AP (PI=7.7)

(20ul)、Marker (5ul)、Positive (200ng)          1-5、AH 1-5 (20ul)、Positive (200ng)

COMPOSITE ADJUVANT SYSTEM AND METHOD FOR PREPARING ADJUVANT

This application is a National Phase application of PCT application no. PCT/CN2020/098012 filed on June 24. 2020, which claims the priority of the Chinese patent application filed with the Chinese Patent Office on Jun. 28, 2019, with the application number CN 201910574668.X and entitled "COMPOSITE ADJUVANT SYSTEM AND METHOD FOR PREPARING ADJUVANT", the entire content of which is incorporated herein by reference.

TECHNICAL FIELD

The present disclosure pertains to the technical field of medicine, and specifically relates to a specific novel adjuvant system including aluminum phosphate (AP) and cytosine-phosphate-guanine oligodeoxynucleotides (CpG ODN).

BACKGROUND

In recent years, with the continuous deepening of immunological research and the rapid development of genetic engineering technology, research of new vaccines such as live vector vaccines, DNA vaccines, and protein vaccines has made a gratifying progress. These new vaccines have high purity, high specificity, but weak immunogenicity, and the immune response induced is not strong enough. Therefore, it is particularly important to use adjuvants to enhance their immunogenicity or enhance protective response of a host to antigens.

An aluminum salt adjuvant is low cost and convenient to use. It is the most widely used adjuvant in the production of biological products. It is also the first adjuvant approved by the U.S. Food and Drug Administration (FDA) for use in human vaccines. Currently, commonly used aluminum adjuvants are mainly aluminum hydroxide adjuvants and aluminum phosphate adjuvants. Aluminum salts have numerous advantages as vaccine adjuvants. In addition to enhancement of the immune response, aluminum salts also have very solid safety data. Although they can effectively induce humoral immune response, they have no obvious effect on cellular immunity and are difficult to induce cellular immune response. As aluminum hydroxide adjuvants and aluminum phosphate adjuvants have different isoelectric points and chemical physical structures, the formulation advantages and adsorption affinity for different vaccine antigens are also different. Some antigens are more suitable for aluminum hydroxide adjuvants, while some are more suitable for aluminum phosphate adjuvants. In the aluminum phosphate adjuvant family, the aluminum phosphate adjuvants having different contents of phosphate radical correspondingly have different isoelectric points.

A novel CpG ODN adjuvant is one of the most prominent vaccine adjuvant technologies in the future. The CpG ODN adjuvant-containing vaccines available from Coley and Dynavax (USA) have entered Phase III clinical trial and have been approved to come into the market, respectively. As a strong immunostimulatory factor for humans and animals discovered so far, CpG ODN is a short single stranded DNA fragment containing short non-methylated nucleotides (cytosine and guanine) as motifs. CpG ODN can not only induce the humoral immune response in the body, but also greatly enhance the cellular immune response thereof, which cannot be achieved only by aluminum adjuvants. Currently, CpG is a novel adjuvant that has been clinically proven to be safe and effective. It can enhance the immunogenicity of vaccines, increase the immune response rate, and stimulate the body to build up more effective immune protection. It is one of the best adjuvant candidates for the development of new vaccines.

To the best of our knowledge, most aluminum compounds used in combination with CpG are aluminum hydroxide adjuvants, while aluminum phosphate adjuvants are rarely used. The aluminum hydroxide adjuvant, presenting in the form of aluminum hydroxyl, is fibrous particles with isoelectric points varying from 10 to 11. It presents in the form of positively charged micron particles in neutral pH solutions (pH 6-7.4), and can sufficiently adsorb negatively charged CpG and negatively charged antigens. The aluminum phosphate adjuvant is a hydroxyl aluminum phosphate complex and is aggregates of spherical particles. The commercial aluminum phosphate adjuvants mostly have isoelectric points around 4-5, and carry negatively charge in the neutral pH solution, which is not conducive to the adsorption of negatively charged CpG. In order to change the poor adsorption capacity of aluminum phosphate adjuvants, some solutions have been proposed in the prior art. For example, in Chinese patent CN106729702, the existing preparation processes and post-treatment processes for aluminum phosphate adjuvants have been investigated and improved to obtain aluminum phosphate adjuvants with improved adsorption capacity and homogeneous appearance morphology. The obtained aluminum phosphate has a particle size that can be effectively controlled between 7.5 and 15 nm and an isoelectric point that can be effectively controlled between 4.0 and 6.0. Consequently, the surface charge and the particle size of the resulting aluminum phosphate adjuvant tend to be homogeneous and the pH value thereof is closer to the pH value of human body fluids.

Vaccine preparations containing adjuvants are all adjuvant-adsorbed antigenic vaccines (antigens in the vaccine are adsorbed on the adjuvant). However, due to the presence of adjuvants, the test of some vaccine quality verification items will be interfered or even impossible to carry out. Therefore, in practice, it is necessary to not only provide an adjuvant system with better desorption effect, but also free the antigens adsorbed on the adjuvant in a certain way for detection and analysis. For example, Chinese Patent 103471902A provides a method of desorption for vaccines containing aluminum phosphate adjuvants, and states that the vaccines containing adjuvants should be dissolved in an alkaline solution, and then neutralized by acidic chemical reagents containing a metal complexing agent. This approach is liable to cause degradation of the antigen and lacks of feasibility. The patent CN1572324A improves the adsorption property of the adjuvant system, and states that for the adjuvant system containing aluminum and CpG adjuvants, the antigen should only be adsorbed on the aluminum adjuvant, but not on the CpG adjuvant, which is an immunostimulant. This adsorption pattern is more beneficial to quality control requirements. In fact, the size of the antigen is hundreds of times that of CpG, and theoretically there is no possibility of antigen adsorption on CpG.

The present disclosure provides a specific novel adjuvant system including an aluminum phosphate adjuvant and a CpG adjuvant. In this adjuvant system, a ratio of phosphate ions to aluminum ions is carefully adjusted, thereby achieving adjustment of the isoelectric point of aluminum adjuvants, control of the adjuvant surface charge, and improvement of the adsorption efficiency for an antigen and CpG. The present disclosure also provides an optimized desorption method, which can give a good antigen desorption efficiency and provide a basis for subsequent evaluation of antigen activity in vitro, and has good commercial value.

SUMMARY

The present disclosure provides an improved adjuvant system containing an aluminum phosphate adjuvant. The inventors of the present disclosure unexpectedly found that, unlike traditional commercial options, selecting an aluminum phosphate adjuvant with an isoelectric point of 7.0 to 9.0, rather than around 4.0 to 6.0, allows the antigen and CpG adjuvant to be adsorbed sufficiently on the aluminum phosphate adjuvant.

It is found in the present disclosure that by joint use of a CpG adjuvant and a specially selected aluminum phosphate adjuvant, a corresponding combined adjuvant system is obtained. This system has a decent ability to adsorb the antigen and CpG, and it also allows the antigen and CpG to be effectively desorbed to obtain an antigen solution. This adjuvant system is advantageous for vaccine preparation and evaluation of content, activity, and the like of the antigen. Specifically, it is found in the present disclosure that when the ratio of aluminum element to phosphorus in aluminum phosphate increases, the adsorption capacity of CpG rises. This is because under the same neutral pH environment, as the ratio of aluminum element to phosphorus in aluminum phosphate increases, the isoelectric point of aluminum phosphate also rises, resulting in an increase in aluminum phosphate surface positive charge. On the other hand, adsorption of the CpG and antigen increases as the content of the aluminum adjuvant (calculated based on the aluminum element content in the adjuvant) increases. The present disclosure further focuses on the finding when a mass ratio of the aluminum element and the CpG content is between 1:4 and 4:1 in the adjuvant, where the CpG can be sufficiently adsorbed on the aluminum phosphate with the antigen has a good desorption effect as well. More preferably, when the mass ratio of aluminum element and CpG in the system is between 1:2 and 2:1, the most favorable adsorption of CpG and the antigen on the aluminum phosphate adjuvant is achieved.

The CpG adjuvant indicated in the present disclosure refers to a DNA fragment containing an unmethylated cytosine-guanine dinucleotide motif. It can activate cells such as B cells, NK, and dendritic cells (DC) and stimulate them to release IL-12 and IFNγ, thereby inducing strong Th1-type response and cellular immunity. As an example, the ideal CpG adjuvant may be CpG7909 (Coley) or CpG 1018ISS (Dynavax), etc.

In the present disclosure, a series of aluminum phosphate adjuvants, of which isoelectric points are greater than that (5.0) of commercial aluminum phosphate adjuvants, are obtained by adjusting the ratio of a soluble aluminum salt, phosphate, and an alkaline solution. More preferably, the aluminum phosphate adjuvant obtained by the inventors of the present disclosure has an isoelectric point between 7.0 and 9.0, preferably between 8.0 and 9.0, and the most preferably between 8.5 and 9.0. On this basis, the inventors of the present disclosure provide a combined adjuvant system containing the aluminum phosphate adjuvant. A method of obtaining the aluminum phosphate adjuvant with isoelectric points between 7.0 and 9.0 provided by the present disclosure is shown as follows:

1) mixing a soluble aluminum salt (preferably $AlCl_3$) and a soluble phosphate ($NaH_2PO_4$, $Na_2HPO_4$, or $Na_3PO_4$) to prepare a solution 1 in which a molar ratio of $PO4^{3-}$ and $Al^{3+}$ is between 1:3 and 1:10;

2) mixing the solution 1 with an alkaline solution (preferably NaOH) to prepare, by precipitating, aluminum phosphate adjuvant under a predetermined pH condition in which a molar ratio of $PO_4^{3-}$ and $Al^{3+}$ is between 1:3 and 1:10; and in a case of using $NaH_2PO_4$, the molar ratio of $PO_4^{3-}$ and $OH^-$ is between 3:5.56 and 10:22.7 to ensure a constant pH; and 3) adsorbing the antigen and CpG to produce a vaccine product of the combined adjuvant system of the present disclosure, or directly combining with a negatively charged CpG to form the combined adjuvant system.

The above method, in another way of expression, involves:

1. mixing a soluble aluminum salt and a soluble phosphate with alkaline solutions of different concentrations;

2. adjusting a ratio of the soluble aluminum salt and the soluble phosphate in the reaction solution, to obtain a series of aluminum phosphate adjuvants with different isoelectric points; and 3. combining the aluminum phosphate adjuvants with a negatively charged CpG adjuvant to form a combined adjuvant system.

In the above, the soluble aluminum salt is $AlCl_3$, the soluble phosphate is $NaH_2PO_4$, $Na_2HPO_4$ or $Na_3PO_4$, the alkaline solution is NaOH, and the pH is 7-12.

In the adjuvant system provided by the present disclosure, the aluminum phosphate adjuvant adsorbs 85-100% of the vaccine antigen and 50-100% of the CpG. More preferably, the aluminum phosphate adjuvant in the system adsorbs 85-100% of the vaccine antigen and 80-100% of the CpG adjuvant. In order to achieve the goal of vaccines antigen quality verification without interference in the detection, the present disclosure creates an optimized desorption method, including the steps of:

1) mixing the above adjuvant system having an antigen adsorbed with a desorption solution and then gently agitating or shaking the resultant for more than 1 hour;

2) directly obtaining a supernatant solution which contains desorbed antigen. Alternatively, centrifugation is properly performed to remove aluminum adjuvant particles that may remain, and then the supernatant solution is obtained. In the above, the preferred desorption solution contains sodium phosphate, sodium citrate, sodium chloride, and Tween 80. A mass ratio of the desorption solution and the desorption sample (that is, the adjuvant system having an antigen adsorbed) is greater than 1:1. Those skilled in the art can understand that a larger volume of the desorption liquid provides a better desorption effect. However, considering factors such as cost, the mass ratio is preferably between 1:1 and 1:3. The above desorption solution may contain 160 mM-220 mM sodium phosphate, 0.2-0.6 M sodium citrate, 0.15-2 M sodium chloride, and 0.01%-0.4% PS-80, and the pH value of the desorption solution is 6-7.

Compared with the existing commercial adjuvants (especially CpG-combined aluminum hydroxide adjuvant), the novel adjuvant system provided by the present disclosure has better adsorption and desorption capabilities (as detailed in the examples). Therefore, the adjuvant of the present disclosure has a wider application and a better immune effect of vaccines.

Other aspects of the present disclosure are apparent to those skilled in the art due to the disclosure herein.

DETAILED DESCRIPTION OF THE EMBODIMENTS

Figure 1:
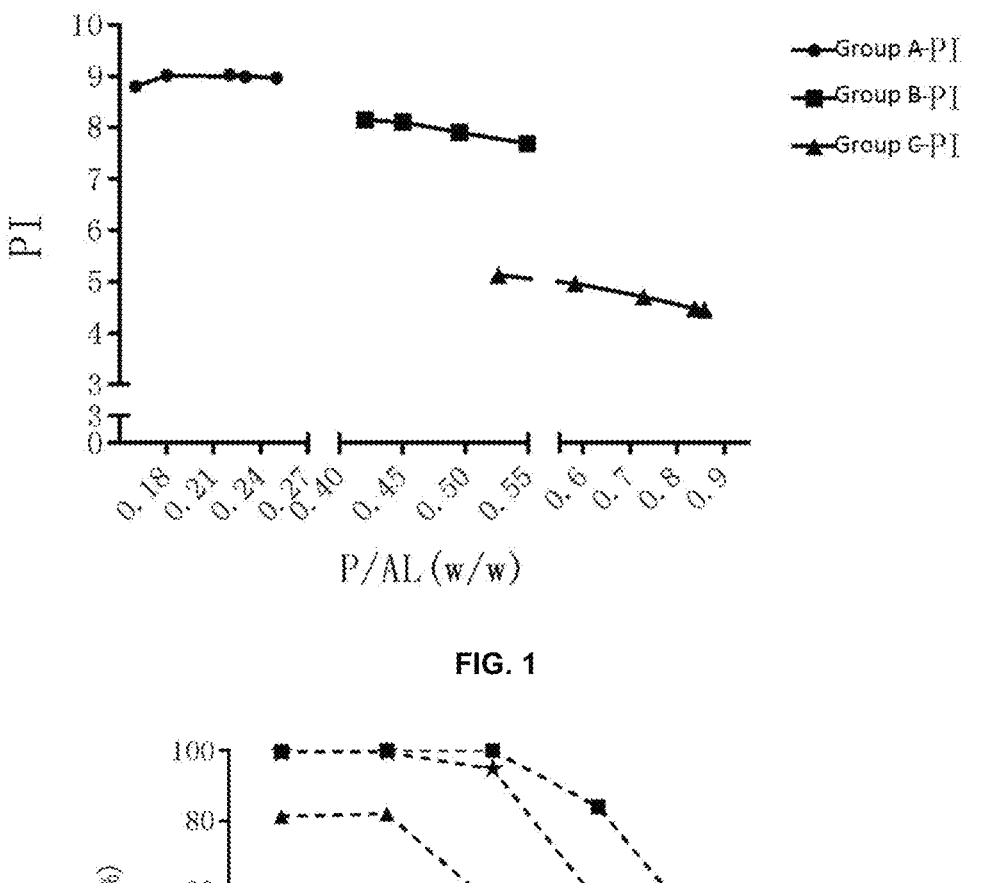
FIG. 1 shows isoelectric points of aluminum phosphate adjuvants with different P/Al ratios, where ● represents the PI value of group A in Table 1; ■ represents the PI value of group B in Table 1; ▼ represents the PI value of group C in Table 1. It should be noted that Al represents aluminum; PI represents isoelectric point; P/Al represents the ratio of phosphorus to aluminum content in aluminum phosphate.

An object of the present disclosure is to prepare an aluminum phosphate (AP) adjuvant with an isoelectric point of 7.0 or greater by adjusting a ratio in a reaction solution, and to apply the aluminum phosphate adjuvant to form a novel adjuvant combination including aluminum phosphate and CpG and having a high adsorption efficiency, so as to change a weak adsorption effect of the commercial aluminum phosphate on CpG, thus changing the current situation where only aluminum hydroxide can be used to adsorb CpG. Meanwhile, the inventors of the present disclosure found that the adjuvant system of the present disclosure has a better ability to desorb antigen than an adjuvant system of an aluminum hydroxide adjuvant that has adsorbed CpG. Also, in the later studies, provided is a new desorption method for the adjuvant system including aluminum phosphate and CpG and having a high adsorption efficiency, which is more conducive to the preparation and evaluation in the field of vaccines, and has a broad application prospect.

EXAMPLE 1. Preparation of the New Adjuvant Complexes Including Aluminum Phosphate and CpG and Having High Adsorption Efficiency

1. Obtaining Aluminum Phosphate Adjuvants With Different Isoelectric Points A reaction solution 1 (a mixed solution of aluminum chloride and sodium dihydrogen phosphate) and a reaction solution 2 (sodium hydroxide solution) were pumped at a certain ratio using a peristaltic pump into a glass reactor with a volume of 600 mL. The compositional ratio of $PO_4^{3-}/Al^{3+}$ and the volume of NaOH added were adjusted, with the detailed information shown in Table 1 below. The reactor was placed on a magnetic stirrer, and the mixed reaction solution was stirred at a constant speed. The suspension was collected and left to stand, then the supernatant was discarded, and the resultant was centrifuged at 8000 rpm for 15 min to obtain the precipitate. The precipitate was dispersed in a certain volume of pure water to obtain an aluminum phosphate adjuvant solution in a certain concentration range.

TABLE 1

Summary of reaction information for aluminum phosphate adjuvants with different isoelectric points

| Groups | Reaction solution 1 (mol/L) | | Reaction solution 2 | Reaction solution 1/Reaction solution 2 |
|---|---|---|---|---|
| | $PO_4^{3-}$ | $Al^{3+}$ | NaOH (mol/L) | Reaction ratio (v/v) |
| Group A | 0.011 | 0.11 | 0.5 | 2:1, 2.25:1, 2.5:1, 2.75:1, 3:1 |
| Group B | 0.03 | 0.09 | 0.5 | 2:1, 2.25:1, 2.5:1, 2.75:1, 3:1 |
| Group C | 0.06 | 0.06 | 0.5 | 2:1, 2.25:1, 2.5:1, 2.75:1, 3:1 |

The prepared aluminum phosphate suspension was sterilized by moist heat sterilization at 121° C. for 30 min. The resultant was then stored at 4° C. The P/Al ratios and isoelectric points of the reaction products were measured. The compositional ratio of $PO_4^{3-}/Al^{3+}$ in the reaction solution 1 and the volume of NaOH added in the reaction solution 2 were adjusted to prepare a series of aluminum phosphate adjuvants with the isoelectric point values ranging from 4.5 to 9.2. The results are shown in FIG. 1.

As can be seen from FIG. 1, when the molar ratio of $PO_4^{3-}$ and $Al^{3+}$ in the reaction solution 1 was between 1:3 and 1:10, and in reaction solution 1 and 2, the molar ratio of $PO_4^{3-}$, $Al^{3+}$ and NaOH solution was between 1:3:5.56 and 1:10:22.7, the prepared aluminum phosphate adjuvants had an isoelectric point of 7.0 or greater. In addition, further studies in the following examples show that an adjuvant system of aluminum phosphate and CpG prepared using the above aluminum phosphate adjuvant with an isoelectric point of 7.0 or greater had decent adsorption and desorption results.

Hereinafter, four aluminum phosphate adjuvants with isoelectric points of 9.0, 8.5, 7.7, and 5.1, respectively, were selected as representatives for subsequent adsorption and desorption studies. It should be noted that when the isoelectric points were 9.0, 8.5, 7.7, and 5.1, respectively, for preparing the above four aluminum phosphate adjuvants, the mass ratio of the P element and the Al element were 0.192, 0.235, 0.495, and 0.526, respectively. The isoelectric point value of the commercial AH used in this study is 11.0.

Figure 2:
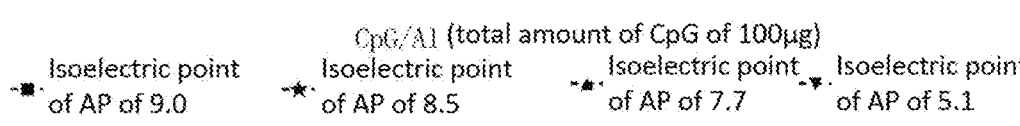
FIG. 2 shows adsorption curves of Al adjuvants with different isoelectric points for CpG. Among them, ■ represents the adsorption effect of AP (aluminum phosphate, isoelectric point of 9.0) prepared in the manner shown in Table 2 for CpG; ▲ represents the adsorption effect of AP (isoelectric point of 7.7) prepared in the manner shown in Table 2 for CpG; and ▼ represents the adsorption effect of AP (isoelectric point of 5.1) prepared in the manner shown in Table 2 for CpG.

2. Adsorption Effect of Aluminum Phosphate Adjuvants With Different Isoelectric Points on CpG The aluminum phosphate adjuvants with PIs of 5.1, 7.7, 8.5, and 9.0 were selected to study the adsorption effect of these adjuvants on CpG. The specific method is shown as follows: a lyophilized powder of CpG was dissolved and diluted to 200 μg/ml in the buffer; and the aluminum adjuvants were subjected to doubling gradient dilution from 800 μg/ml to 50 μg/ml. Each gradient dilution sample of the aluminum adjuvant and the CpG diluent were added in equal volume. The mass ratio of the CpG and the aluminum element in the aluminum adjuvant is shown in Table 2. Subsequently, the above solution was mixed for 4 hours and centrifuged to obtain a supernatant, and the CpG adsorption efficiency was calculated by the UV-MCA method. The results are shown in FIG. 2.

TABLE 2

Preparation ratio of CpG and gradient solutions of aluminum adjuvants (AP with PIs of 5.1, 7.7, 8.5, and 9.0, respectively)

| CpG (μg/ml) | Al (μg/ml) | CpG/Al (v/v) | Determination method |
|---|---|---|---|
| 200 | 800 | 1:4 | UV-MCA method |
| 200 | 400 | 1:2 | |
| 200 | 200 | 1:1 | |
| 200 | 100 | 2:1 | |
| 200 | 50 | 4:1 | |

It can be seen from FIG. 2 that the adsorption capacity for CpG depends on the isoelectric point of the aluminum adjuvant (AP) and the ratio of CpG to Al. It can be seen from FIG. 2 that the common aluminum phosphate adjuvant (with an isoelectric point of about 5.0) in the prior art has an unsatisfactory adsorption effect on CpG. When the isoelectric point is 7.0 or greater, the adsorption effect of the aluminum phosphate adjuvant for the CpG adjuvant is greatly improved (dozens of times). It has an unexpected technical effect, which is comparative with the commonly used aluminum hydroxide adjuvant. Furthermore, when the isoelectric point is between 8.5 and 9.0, a better and unexpected effect in terms of the adsorption efficiency of the aluminum phosphate for CpG is obtained in the improved adjuvant system provided by the present disclosure.

It can be seen that the aluminum phosphate adjuvants of different PIs can be prepared by adjusting the compositional ratio of $PO_4^{3-}/Al^{3+}$ and the volume of NaOH added in the reaction. The AP aluminum adjuvants with PIs greater than 7.7 have a better adsorption effect on CpG and can replace the aluminum hydroxide adjuvant and form a novel aluminum phosphate-CpG adjuvant combination.

EXAMPLE 2. Application of Aluminum Phosphate and CpG Adjuvant to gE Immune Vaccine The adsorption effect of the aluminum phosphate adjuvants with PIs of 7.7, 8.5, and 9.0 for CpG and a gE antigen: a stock solution of the gE antigen was first adsorbed onto the aluminum adjuvant to prepare an adsorption sample with a ratio of gE antigen/Al (w/w) being 200 μg/1200 μg/ml, then, to the gE antigen/Al adsorption sample were added CpG samples of different concentrations: 1) 0 μg/ml, 2) 100 μg/ml, 3) 200 μg/ml, 4) 300 μg/ml, 5) 500 μg/ml, 6) 600 μg/ml, 7) 900 μg/ml, and 8) 1200 μg/ml, after adsorption for 24 h, the resultants were centrifuged to obtain supernatants, and the respective adsorption effects for CpG and gE were calculated by western-blot and UV second-order derivative.

Figure 3:
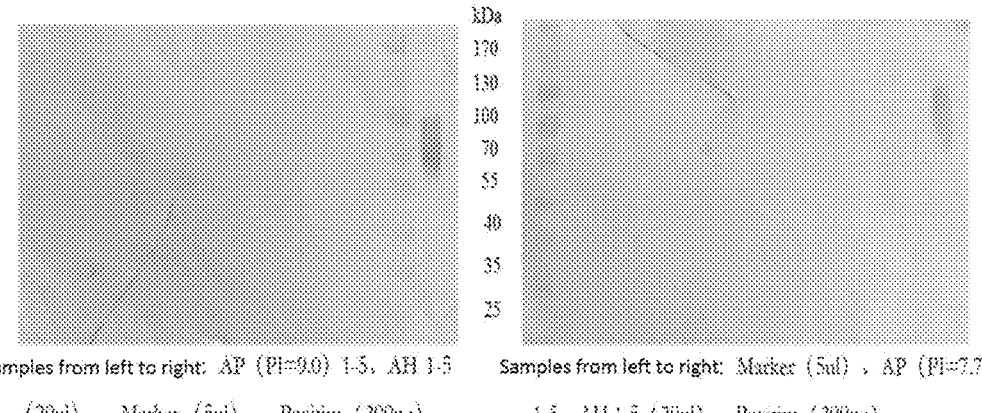
FIG. 3 shows the gE content in a supernatant after Al adsorbs gE antigen protein and CpG in a Western-blot assay. In the figure, samples from left to right in the left drawing are: AP (PI=9.0, lanes 1-5 corresponding to different ratios), AH (aluminum hydroxide, lanes 6-10 corresponding to different ratios), Marker, and a positive control. Samples from left to right in the right drawing are: Marker, AP (PI=7.7, lanes 1-5 corresponding to different ratios) 1, AH (aluminum hydroxide, lanes 6-10 corresponding to different ratios), Marker, a positive control.

From experimental results shown in FIG. 3, it is found that, after the aluminum phosphate adjuvant system with a PI greater than 7.7 adsorbed the antigen, the concentration of free gE antigen in the preparation after adsorption was less than 10 μg/ul, and the total protein concentration of the gE antigen was 100 μg/μl. It can be seen that the aluminum phosphate adjuvant system provided by the present disclosure should have an adsorption efficiency of over 90% for the gE antigen in the presence of CpG, and the increase of CpG content will not reduce the adsorption efficiency of the aluminum adjuvant for the gE antigen.

Figure 4:
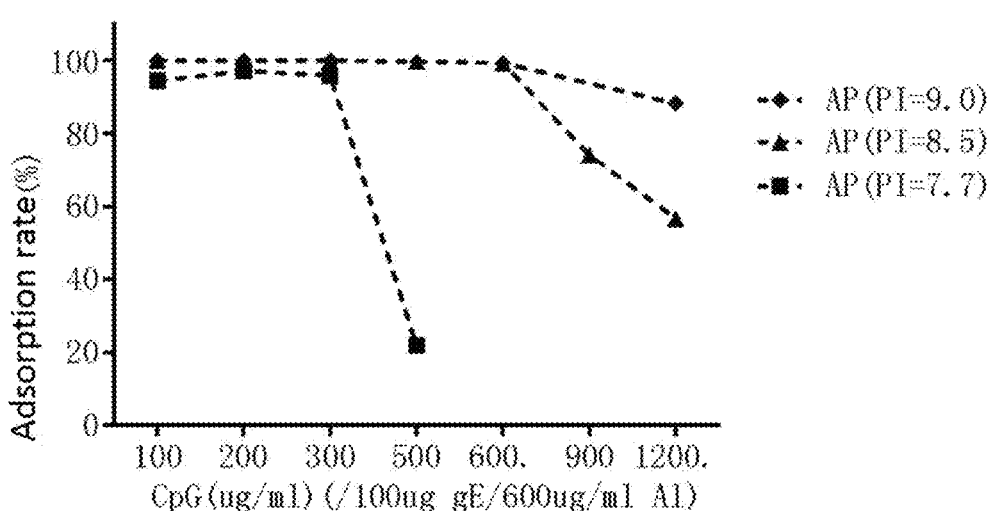
FIG. 4 shows adsorption efficiencies of different concentrations of CpG after CpG is adsorbed by sample (100 μg of gE/600 μg of Al/mL). Among them, ▲ represents AP (PI=8.5); ■ represents AP (PI=7.7).

According to the WB results, the amount of the gE antigen in the supernatant of the sample after adsorption was less than 10 μg/ml, and thus the UV absorption value of the supernatant basically reflected the amount of CpG. The adsorption curves of the aluminum phosphate (AP) adjuvants that have adsorbed the gE antigen stock solution for the CpG adjuvant, as determined by the UV second-order derivative method, are shown in FIG. 4. It can be seen from FIG. 4 that the dual-adjuvant system of the aluminum phosphate (isoelectric point of between 7.0 and 9.2) and CpG provided by the present disclosure has good adsorption capacity for antigen, and the increase of CpG content will not reduce the adsorption efficiency of the aluminum adjuvant for the gE antigen.

EXAMPLE 3. Antigen Desorption Method

1) Screening of Type of Desorption Solution

Into an adsorption sample with a ratio of gE/Al (Al element in the aluminum adjuvant) (w/w) (AH adjuvant) reaching 200 μg/1200 μg/ml, desorption solution was added at a ratio of 1:3 under desorption condition as shown in following Table 3. After desorption at 25 degrees Celsius for 2 h, 24 h, and 48 h, the supernatant was obtained by centrifuging, and the gE content was detected by the UV second-order derivative to calculate the recovery rate. The results are shown in FIG. 5.

Into an adsorption sample with the ratio of CpG/Al (w/w) (AH adjuvant) being 600 μg/1200 μg/ml, desorption solution was added at a ratio of 1:3. After desorption at 25 degrees Celsius for 2 h, 24 h, and 48 h, the supernatant was obtained by centrifuging, and then the CpG content was detected by the UV second-order derivative to calculate the recovery rate. The results are shown in FIG. 5.

Figure 5:
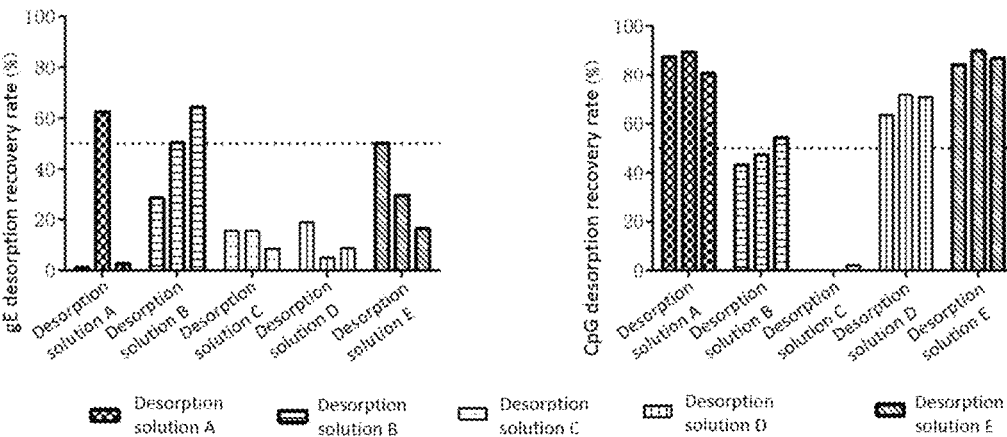
FIG. 5 shows desorption recovery rates of gE and CpG adsorbed by an AH adjuvant under the action of different desorption solutions (desorption solutions A-E) after desorbed for 2 hours, 24 hours and 48 hours.

Data in FIG. 5 show that a desorption solution E has a good desorption effect for both the gE protein and the CpG adjuvant.

TABLE 3

Screening of compositions of different desorption solutions

| | Compositions of desorption solutions | Desorption ratio (adsorption sample/ desorption solution) |
|---|---|---|
| A | 1.2M potassium phosphate, pH = 7.0 (method provided by Desorption of porcine parvovirus from aluminum hydroxide adjuvant with subsequent viral immunoassay or hemagglutination assay, VetRes Commun. 1987, 11(1): 83-92) | 1:3 |
| B | 1.25 ml of 20% diethanol amine and 0.20 ml of 10% Triton X-100, into which 8.55 ml of PBS was added and mixed homogenously, pH = 11.0 (method provided by pharmacopeia) | 1:3 |
| C | 200 mM citric acid-sodium citrate buffer, pH = 3 | 1:3 |
| D | 20% (w/v) trisodium citrate | 1:3 |
| E | 200 mM sodium phosphate, 0.2M sodium citrate, 2M sodium chloride, pH 6.7 | 1:3 |

2) The surfactant Has a Protective Effect on the Desorbed gE Antigen

For a dissociation solution A and a dissociation solution E, in which 0.4% PS-80 was selected and added to their

9

Figure 6:
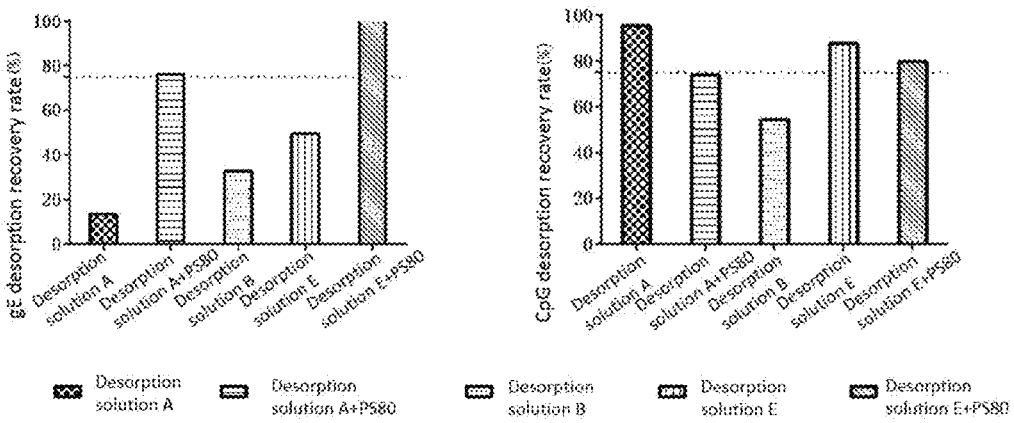
FIG. 6 shows an effect of PS-80 on a desorption recovery rate of gE and CpG adsorbed by the AH adjuvant after desorbed for 3 hours.

10 compositions, and a dissociation solution B containing Triton X-100 surfactant, the above-mentioned desorption experiment of the adjuvants was repeated. After desorption at 37 degrees Celsius for 3 h, the supernatant was obtained by centrifuging, and the CpG content was detected by the UV second-order derivative to calculate the recovery rate. The results shown in FIG. 6 showed that, compared with the conventional Triton X-100 surfactant, PS-80 surfactant has a better protective effect on desorbed antigen.

3) Investigation of gE Antigen Desorption Effect of Aluminum Hydroxide and Aluminum Phosphate Adjuvants Under the Same Desorption Condition According to the above experiment, the desorption solution E was finally used for desorption, and PS-80 surfactant was added. On this basis, the gE antigen desorption effects of the aluminum hydroxide and aluminum phosphate adjuvants under the same desorption condition were further studied.

Figure 7:
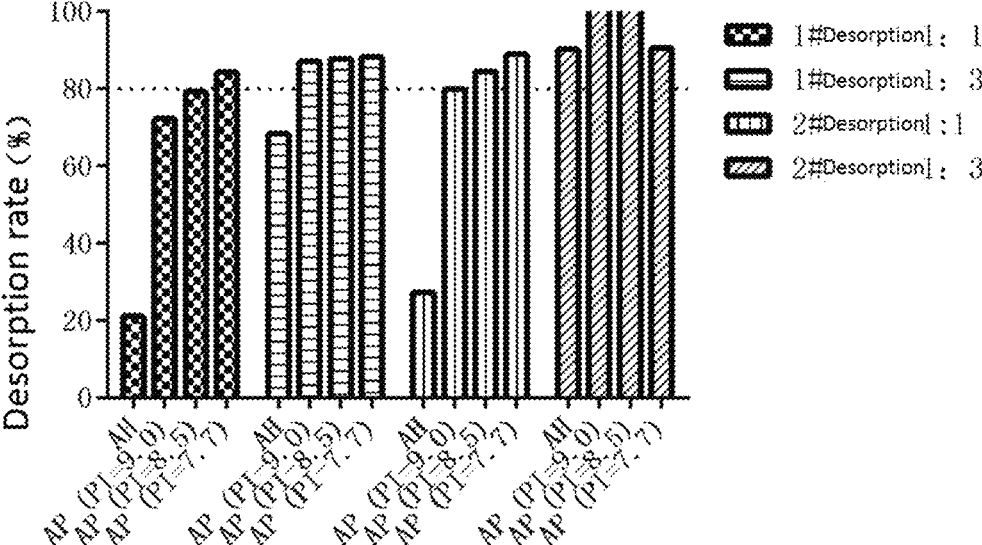
FIG. 7 shows comparison of desorption effects of different aluminum adjuvants (AP and AH) that have adsorbed gE sample.

For a sample after desorbed under the desorption condition for gE vaccine shown in Table 4 below for 24 hours, it can be observed that only a small amount of residue was present at the bottom for the AP adjuvant sample after centrifugation, while a large amount of white solid was present at the bottom for the aluminum hydroxide adjuvant sample after centrifugation. By comparing the gE desorption efficiencies of different aluminum adjuvants under the same desorption condition in FIG. 7, it can be seen that the gE desorption recovery rate of the aluminum hydroxide adjuvant adsorption sample is lower than the gE desorption recovery rate of the aluminum phosphate adjuvant adsorption sample. The desorption effect is better when the desorption ratio of adsorption sample/desorption solution is 1:3. It can be seen that the novel adjuvant provided by the present disclosure has better desorption capacity than that of the existing commercial combined adjuvant of CpG and aluminum hydroxide.

TABLE 4

Desorption conditions for the samples of aluminum hydroxide, aluminum phosphate (AP, PI = 7.0, 8.5, or 9.0) adjuvants that have adsorbed gE

| Composition of desorption solution | Desorption ratio (adsorption sample/ desorption solution) | Desorption temperature and duration |
| --- | --- | --- |
| 1#: 200 mM sodium phosphate, 0.2M sodium citrate, 2M sodium chloride, 0.4% PS-80, pH 6.7 | 1:1 1:3 | 25 degrees Celsius for 24 h |

TABLE 4-continued

Desorption conditions for the samples of aluminum hydroxide, aluminum phosphate (AP, PI = 7.0, 8.5, or 9.0) adjuvants that have adsorbed gE

| Composition of desorption solution | Desorption ratio (adsorption sample/ desorption solution) | Desorption temperature and duration |
| --- | --- | --- |
| 2#: 160 mM sodium phosphate, 0.2M sodium citrate, 2M sodium chloride, 0.4% PS-80, pH 6.7 | 1:1 1:3 | |

All the documents mentioned in the present disclosure are cited as references in this application, as if each document is individually cited as a reference. In addition, it should be understood that after reading the above teaching of the present disclosure, those skilled in the art can make various changes or modifications to the present disclosure, and these equivalent forms also fall within the scope defined by the appended claims of the present application.

The invention claimed is:

1. An antigen desorption method for a combined adjuvant system comprising an aluminum phosphate adjuvant and a CpG adjuvant, wherein the aluminum phosphate adjuvant has an isoelectric point between 7.0 and 9.0, and the antigen desorption method comprises steps of:
   1) mixing the combined adjuvant system that adsorbed an antigen with a desorption solution and then shaking a resultant gently for more than 1 hour;
   2) obtaining a dissolved sample solution or supernatant to obtain desorbed antigen solution,
   wherein the desorption solution contains 160 mM-220 mM sodium phosphate, 0.2-0.6 M sodium citrate, 0.15-2 M sodium chloride, and 0.01-0.4% PS-80, and the pH is 6-7.

2. The method according to claim 1, wherein the CpG adjuvant is CpG7909.

3. The method according to claim 1, wherein the aluminum phosphate adjuvant in the adjuvant system can adsorb both vaccine antigen and CpG adjuvant.

4. The method according to claim 1, wherein the aluminum phosphate adjuvant in the adjuvant system can adsorb 85-100% of the vaccine antigen and 50-100% of the CpG adjuvant.

5. The method according to claim 4, wherein the aluminum phosphate adjuvant in the adjuvant system can adsorb 85-100% of the vaccine antigen and 80-100% of the CpG adjuvant.

6. The method according to claim 3, wherein the weight ratio of an aluminum element of the aluminum phosphate adjuvant and CpG is that the aluminum element: CpG=1:4-4:1.

7. The method according to claim 1, wherein the weight ratio of an aluminum element of the aluminum phosphate and CpG is 1:2-2:1.

8. The method according to claim 1, wherein the aluminum phosphate adjuvant has an isoelectric point between 8.0 and 9.0.

* * * * *